United States Patent
Bonnet et al.

(10) Patent No.: US 11,484,272 B2
(45) Date of Patent: Nov. 1, 2022

(54) ACTIVE IMPLANTABLE MEDICAL DEVICE THAT CAN PERFORM A FREQUENTIAL ANALYSIS

(71) Applicants: SORIN CRM SAS, Clamart (FR); INSERM—INSTITUT NATIONAL DE LA SANTE ET DE LA RECHERCHE MEDICALE, Paris (FR); UNIVERSITE DE RENNES 1, Rennes (FR)

(72) Inventors: Jean-Luc Bonnet, Massy (FR); Thomas Herrmann, Paris (FR); Christine Henry, Paris (FR); Alfredo Hernandez, Cesson Sévigné (FR); Guy Carrault, Cesson Sévigné (FR)

(73) Assignees: SORIN CRM SAS, Clamart (FR); INSERM—INSTITUT NATIONAL DE LA SANTE ET DE LA RECHERCHE MEDICALE, Paris (FR); UNIVERSITE DE RENNES 1, Rennes (FR)

(*) Notice: Subject to any disclaimer, the term of this patent is extended or adjusted under 35 U.S.C. 154(b) by 424 days.

(21) Appl. No.: 15/765,196

(22) PCT Filed: Sep. 30, 2016

(86) PCT No.: PCT/EP2016/073515
§ 371 (c)(1),
(2) Date: Mar. 30, 2018

(87) PCT Pub. No.: WO2017/055608
PCT Pub. Date: Apr. 6, 2017

(65) Prior Publication Data
US 2018/0271452 A1 Sep. 27, 2018

(30) Foreign Application Priority Data

Oct. 1, 2015 (FR) ...................................... 1559320

(51) Int. Cl.
*A61B 5/00* (2006.01)
*G16H 40/40* (2018.01)
(Continued)

(52) U.S. Cl.
CPC .......... *A61B 5/7257* (2013.01); *A61B 5/0245* (2013.01); *A61B 5/076* (2013.01);
(Continued)

(58) Field of Classification Search
CPC .............. A61B 5/7257; A61B 5/04001; A61B 5/04012; A61B 5/0432; A61B 5/0456;
(Continued)

(56) References Cited

U.S. PATENT DOCUMENTS

| 4,404,972 A | 9/1983 | Gordon et al. |
| 7,186,220 B2 | 3/2007 | Stahmann et al. |

(Continued)

FOREIGN PATENT DOCUMENTS

| FR | 2492262 | 4/1982 |
| WO | WO-91/19452 | 12/1991 |

OTHER PUBLICATIONS

Search Report on French Application No. 1559320 dated Jun. 7, 2016. 4 pages.
(Continued)

*Primary Examiner* — Jon Eric C Morales
(74) *Attorney, Agent, or Firm* — Foley & Lardner LLP (57) ABSTRACT

The invention relates to an active implantable medical device comprising a processing unit able to be alternately operated during a predetermined period of activity and on standby during a standby period in a cyclical manner, and means for acquiring data relating to physiological and/or physical activity. The device also comprises means for calculating a frequency analysis of the data acquired, said
(Continued)

calculating means being capable of successively perform part of the frequency analysis during periods of activity of the processing unit.

13 Claims, 4 Drawing Sheets

(51) Int. Cl.

| | | |
|---|---|---|
| *G06F 1/3206* | (2019.01) | |
| *G06F 1/3287* | (2019.01) | |
| *G06F 1/329* | (2019.01) | |
| *A61B 5/07* | (2006.01) | |
| *A61N 1/37* | (2006.01) | |
| *A61B 5/24* | (2021.01) | |
| *A61B 5/316* | (2021.01) | |
| *A61B 5/333* | (2021.01) | |
| *A61B 5/352* | (2021.01) | |
| *A61B 5/363* | (2021.01) | |
| *A61B 5/364* | (2021.01) | |
| *A61B 5/389* | (2021.01) | |
| *G16H 50/20* | (2018.01) | |
| *A61B 5/0245* | (2006.01) | |
| *A61B 5/08* | (2006.01) | |
| *A61B 5/11* | (2006.01) | |
| *A61B 5/024* | (2006.01) | |

(52) U.S. Cl.
CPC .......... *A61B 5/0816* (2013.01); *A61B 5/1107* (2013.01); *A61B 5/1118* (2013.01); *A61B 5/24* (2021.01); *A61B 5/316* (2021.01); *A61B 5/333* (2021.01); *A61B 5/352* (2021.01); *A61B 5/363* (2021.01); *A61B 5/364* (2021.01); *A61B 5/389* (2021.01); *A61B 5/4836* (2013.01); *A61B 5/4839* (2013.01); *A61B 5/686* (2013.01); *A61B 5/726* (2013.01); *A61B 5/7285* (2013.01); *A61N 1/3702* (2013.01); *G06F 1/3206* (2013.01); *G06F 1/329* (2013.01); *G06F 1/3287* (2013.01); *G16H 40/40* (2018.01); *G16H 50/20* (2018.01); *A61B 5/02405* (2013.01); *A61B 5/4035* (2013.01); *A61B 2560/0204* (2013.01); *A61B 2560/0209* (2013.01)

(58) Field of Classification Search
CPC ... A61B 5/0464; A61B 5/0468; A61B 5/0488; A61B 5/076; A61B 5/0816; A61B 5/1107; G06F 1/3206; G06F 1/3287; G06F 1/329
USPC ......................................................... 600/301
See application file for complete search history.

(56) References Cited

U.S. PATENT DOCUMENTS

| | | |
|---|---|---|
| 2007/0255331 A1 | 11/2007 | Gillberg et al. |
| 2007/0260285 A1* | 11/2007 | Libbus .................. A61B 5/318 607/9 |
| 2014/0088379 A1 | 3/2014 | Irazoqui et al. |
| 2015/0257669 A1 | 9/2015 | Ben-David et al. |
| 2016/0213261 A1* | 7/2016 | Fleischer ............. A61B 5/7275 |
| 2018/0125418 A1* | 5/2018 | Haakma ............... A61B 5/4812 |

OTHER PUBLICATIONS

International Search Report and Written Opinion on International Application No. PCT/EP2016/073515 dated Apr. 6, 2017. 10 pages.

* cited by examiner

Fig.10

ACTIVE IMPLANTABLE MEDICAL DEVICE THAT CAN PERFORM A FREQUENTIAL ANALYSIS

CROSS-REFERENCE TO RELATED APPLICATIONS

This application is a 371 U.S. National Application of International Application No. PCT/EP2016/073515, filed Sep. 30, 2016, which claims the benefit of and priority to French Patent Application No. 1559320, filed Oct. 1, 2015, which is incorporated herein by reference in its entirety.

BACKGROUND

The invention generally relates to "active implantable medical devices" as defined by the Council of the European Communities directive 90/385/EEC of 20 Jun. 1990.

This definition includes in particular cardiac implants responsible for monitoring cardiac activity and generating pacing, defibrillation and/or resynchronization pulses in case of heart rate disorder detected by the apparatus. It also includes neurological devices, cochlear implants, delivery pumps for medical substances, implanted biological sensors, etc.

These devices comprise a housing generally called "generator", electrically and mechanically connected to one or more "probes" provided with electrodes intended to come into contact with the tissues on which it is desirable to apply stimulation pulses and/or collect an electrical signal: myocardium, nerve, muscle . . . .

The invention more particularly relates to an active implantable medical device able to receive signals collected by probes or delivered by sensors, and to analyze these signals.

Most of the active implantable medical devices include the ability to transmit, especially to an external device, physiological signals such as an electrocardiogram (ECG), or an electroneurogram (ENG), or an electromyogram (EMG), signals relating to the ventilation flow or the acceleration of the heart rate that were previously collected and stored so as to analyze these signals.

In particular, the electrocardiogram-ECG signals provide data indicative of the cardiac activity, in particular the heart rate. The heart rate is a qualitative notion representative of the way the cycles succeed one another. The heart rate is defined by the cardiac electrical activity causing the contraction of the myocardium.

The electrocardiogram-ECG signals, when viewed as a function of time, provide an image of the rhythmic activity of the heart. Problems associated with the heart activity are usually detected based on electrocardiogram-ECG signals.

The rhythmic analysis of the heart of patients having an implanted device is carried out, for example, based on the data of the electrocardiogram ECG signal stored in the device and analyzed by this device. These data can be transmitted to an external device used by cardiologists, in order to be displayed and analyzed, for real-time or deferred analysis.

Physiological signals provide relevant information about the physiological state of one or more organs of the patient. In particular, the heart rate contains information on the autonomous nervous system, in particular about its interrelation with the cardiovascular system. This information can be contained in the frequency spectrum of the physiological signals. A frequency analysis is then used to obtain information relating to the physiological state of one or more organs, individually or in interaction.

Various methods are known for performing a frequency analysis (FA) of physiological signals, one of which consists in performing a Discrete Fourier transform. Another method of frequency analysis consists in performing a Fast Fourier Transform (FFT) in order to exploit some optimizations of the operation of the Discrete Fourier transformation.

Another known method is to carry out scale analyses called wavelet analysis, for example by discrete wavelet analyses. These methods also have a quick calculation version.

Frequency analyses are mainly implemented in systems having a microprocessor or microcontroller that is not limited by power consumption, especially a computer, for which fast and continuous processing is fundamental.

For example, it is known from WO 91/19452 how to use of Fast Fourier Transformation (FFT) for analyzing signals from the electrocardiogram by using an external computer after acquisition of the signals from the patient for the diagnosis of cardiac arrhythmias.

In addition, various solutions have been proposed for analyzing the signals delivered by a fast Fourier transformation. Indeed, it is known, on the one hand, to use a dedicated circuit also called digital signal processor and, on the other hand, to use a standard microprocessor capable of processing high level calculations. However, these two solutions have disadvantages.

Indeed, it is known, in particular from U.S. Pat. No. 7,186,220, of a solution consisting of using a dedicated circuit, that is to say a microprocessor optimized to execute digital signal processing applications. This solution allows fast calculation but implies, when implanted in an autonomous implantable medical device, several difficulties to solve. First, such an implantation requires a large physical location whereas the size of the implantable medical device is crucial and should be as small as possible. In addition, the high energy consumption of dedicated circuits has an impact on the lifetime of these implantable medical devices. Active implantable medical devices that must be as small as possible for an implantation into the human body cannot accommodate such a circuit. Thus, the solution consisting in implementing a dedicated circuit in such an implantable medical device requires too much space and consumes energy insofar as the processing is carried out continuously.

Another solution consisting in using a standard microprocessor or microcontroller, that is to say that is used to perform the usual functions of the implantable system, avoids making hardware modifications for implementing frequency analysis. However, these microprocessors or microcontrollers have limited performance in terms of calculating power. For example, the calculation complexity of a fast Fourier transform varies according to O(n·log n). Such calculations require a very large number of calculation cycles of a microprocessor or a microcontroller.

Thus, calculation for a frequency analysis requires a large amount of energy and a powerful calculating unit, these prerequisite criteria are not met by active implantable medical devices.

SUMMARY

One of the aims of the invention is to propose a solution to these difficulties by using an active implantable medical device to perform a frequency analysis of the signals, in particular by a Fourier transformation, within the medical device without modifying its architecture, whether hardware or software.

To that end, the invention proposes an active implantable medical device comprising a processing unit able to be alternately operated during a determined period of activity and in standby during a standby period, in a cyclical manner, and means for acquiring data related to physiological and/or physical activity.

Typically, the device further comprises means for calculating a frequency analysis of the acquired data, said calculating means being adapted to successively execute a portion of the frequency analysis during periods of activity of the processing unit.

According to various subsidiary features:
- the calculating means are implemented during the period of activity of the processing unit after execution of the standard processing functions executed during the period of activity of the processing unit.
- the calculating means execute a portion of the frequency analysis after execution of the standard processing functions executed until the end of the period of activity of the processing unit.
- said calculating means execute a portion of the frequency analysis for a predetermined duration.
- the device further comprises means for optimizing the frequency analysis by fractioning the frequency analysis into a plurality of elementary modules, the calculating means successively executing the elementary modules during periods of activity of the processing unit.
- the means for optimizing the frequency analysis are also able to select at least one frequency band to be processed.
- the device further comprises means for selecting a period of acquisition of said data.
- the means for selecting an acquisition period furthermore comprise means for verifying the conformity of predetermined criteria.
- the means for acquiring data are implemented when the period of acquisition is reached and the criteria are in accordance with predetermined values.
- the device further comprises means for detecting a determined physiological event external to the device and means for starting the cycle capable of starting the cycle when the detection means detect a specific physiological event.
- the device further comprises means for preprocessing the acquired data.
- the preprocessing means are capable of interpolating and resampling the acquired data.
- the calculating means are implemented in a final portion of the period of activity of the processing unit.
- the frequency analysis is a Fourier transformation.
- the preprocessing means are able to select a subset of the acquired data.
- the preprocessing means are able to filter the acquired data.
- the acquired signal is the electrocardiogram (ECG).
- the acquired signal is the endocavitary electrogram (EGM).
- the acquired signal is the time interval between two consecutive cardiac events.
- the signal of a cardiac endocavitary accelerometer (EA).
- the acquired signal is the electroneurogram (ENG).
- the acquired signal is the electromyogram (EMG).
- the acquired signal is the ventilation.
- the acquired signal is the gastric contraction.
- the acquired signal is a signal of physical activity such as acceleration.
- the frequency analysis is performed by Fast Fourier Transformation (FFT).
- the frequency analysis is a spectral power analysis.
- the frequency analysis is substituted by a wavelet analysis.

BRIEF DESCRIPTION OF THE DRAWINGS

An embodiment of the device of the invention will now be described with reference to the appended drawings.

DETAILED DESCRIPTION

Figure 1:
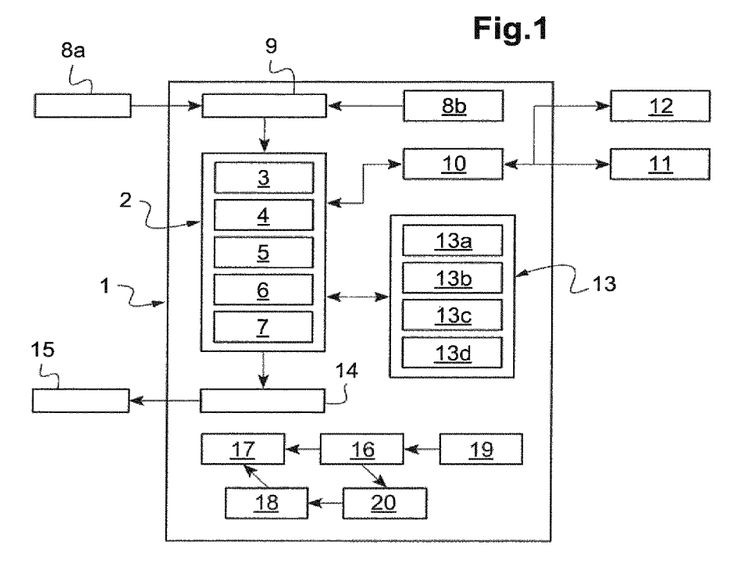
FIG. 1 is a general view of a presentation of an active implantable medical device.

An active implantable medical device 1 is illustrated in FIG. 1. This device comprises a processing unit 2, in particular a processor, a microprocessor or a microcontroller comprising an internal working memory 3.

The processing unit comprises its own clock 4 the frequency of which determines the operating speed of the processing unit. The latter furthermore comprises, for example, standard algorithms 5, in particular the management of the bradycardia and tachycardia episodes, a frequency analysis algorithm 6, a serving algorithm 7, etc.

At least one sensor 8a or 8b for physiological and physical parameters, such as cardiac bypass, heart rate, etc., such as the accelerometer enabling to know the physical activity, the position and the cardiac activity of the patient, is connected for example to a sensor processing unit 9 of the active implantable medical device 1 in order to transmit to the medical device physiological or physical data captured from the patient.

Other sensors can also be implanted within the patient, for example to collect an endocavitary electrogram (EGM), an electroneurogram (ENG), an electromyogram (EMG), a cardiac contractility signal such as endocavitary acceleration (EA), a gastric contractility signal, or any other physiological or physical signal such as the body acceleration signal.

In addition, the active implantable medical device 1 may comprise a telemetry system incorporating an internal communication device 10, for example of the inductive communication or radio frequency (RF) type enabling a communication with an external device 11, in particular a computer or any other device such as a monitoring system 12.

The active implantable medical device 1 further comprises a storage memory device 13 comprising a storage space for storage of various data, for example raw data 13*a*, sampled data 13*b*, temporary data 13*c* or data 13*d* that have been processed.

Such an active implantable medical device 1 may also comprise an interaction system 14 with an external device 15, the interaction system being able to deliver the adapted therapy requested by the external device 15, this therapy can be, for example, the cardiac pacing or the drug delivery through a pump.

Recurrently, the processing unit of the active implantable medical device is able to be operated alternately during a specific period of activity and in standby during a standby period.

According to the invention, the period of activity is of fixed and predetermined or variable duration and the standby period is of fixed or variable duration depending on the physiological activity.

The duration of the period of activity added to the duration of the standby period corresponds to the total duration of a cycle.

According to the invention, the cycle can be regular or irregular.

For example, in a cardiac application, the cycle is a function of the cardiac activity of the patient. On the other hand, in the case of an electromyogram (EMG), the duration of the periods of activity and standby periods can be fixed in advance.

According to a particular embodiment, the cycle corresponds to the cardiac cycle of the patient. Thus, the processing unit is in a standby state and is operated at each cardiac cycle, for example at each beginning of the cardiac cycle. According to this embodiment, there is synchronization of the activation of the processing unit of the active implantable medical device with a cardiac event.

To do this, the medical device comprises means for detecting a determined physiological event external to the device and means for starting the cycle capable of starting the cycle when the detection means detect a specific physiological event, for example the beginning of the cardiac cycle.

The processing unit is then in operation during a determined period of activity.

According to an exemplary embodiment, the activity period is the refractory period, that is to say the period which immediately follows the activity of a cardiac event.

According to an illustrative example, when the heart rate is 60 beats per minute, then the cardiac cycle is 1000 milliseconds. The processing unit is operated at each beginning of the cardiac cycle for a determined duration, for example 16 milliseconds.

According to another illustrative example, the processing duration is variable depending on the calculation load required for the cycle, within the limit of a maximum value, in particular in order not to exceed the cardiac refractory period.

An example of a cyclic mode of operation of the processing unit is detailed in the document FR2492262.

Thus, according to the invention, the processing unit is only used for a few milliseconds per cycle, which has the advantage of a very low energy consumption per cycle, since the processing unit is in a standby state for the majority of the time. The energy consumption and thus the use of the battery of the implantable medical device is distributed over a fraction of each cycle.

During the period of activity of the processing unit, it performs standard processing functions. The execution of these standard processing functions is performed for a non-constant duration, the execution duration being dependent on the data captured from the patient and the execution time of the standard functions.

According to the invention, the active implantable medical device comprises data acquisition means 16 related to the physiological activity.

The physiological activity is for example the heart rate of the patient. However, the physiological activity may be a signal related to the ventilation, an electroneurogram, an electromyogram, an electrocardiogram, an acceleration or any other physiological or physical signal related to the patient.

To do this, the acquisition means can obtain the data related to the physiological activity of the patient via for example the sensors 8*a* or 8*b* connected to the active implantable medical device 1. The data acquisition is carried out for example at a particular moment of the day or the week.

In addition, according to the invention, the active implantable medical device comprises means 17 for calculating a frequency analysis. These calculating means are for example the calculation of a Fourier transform, a Wavelets analysis or a time-frequency analysis. The calculating means 17 perform the calculations from the data acquired in order to perform an analysis of these data.

In order to be able to perform a frequency analysis in such an active implantable medical device while maintaining the lifetime of the device and these main functions, it comprises calculating means 17 able to execute successively a portion of the frequency analysis during periods of activity of the processing unit 2.

Thus, according to the invention, the frequency analysis of the data is split so as to be executed by portion or fragment during periods of activity of the processing unit.

An optimized frequency analysis will now be described in accordance with the invention.

The fragmented execution of the frequency analysis by the active implantable medical device is detailed below and illustrated in FIG. 2. The temporal sequencing of the frequency analysis of data is also illustrated in FIG. 3.

This analysis begins with a step 21 which is a step of selecting a data acquisition period related to the physiological and/or physical activity of the patient and/or to external data. For example, the selection of an acquisition period is related to cardiac activity and/or physical activity of the patient.

A data acquisition period is for example according to a predetermined time information.

During this step, the conformity of predetermined criteria can also be verified, these criteria being in particular physiological conditions.

An example of a criterion is the absence of physical activity of the patient during the acquisition of the data, the physical activity being notably measured from the accelerometer sensor (G) and the heart rate.

The criteria may also correspond to periods of physical activity of the patient, for example in the case of the electromyogram.

Other examples of predetermined criteria are the lack of stimulation by the device and the absence of cardiac arrhythmia.

The criterion can also be based only on the time of the day, for example to record a signal at a given, predetermined time.

This step is illustrated in FIG. 3 by the reference 31.

When the data acquisition period is reached and the predetermined criteria are met then step 21 is followed by a data acquisition step 22. The acquisition of the data is performed in particular by the data acquisition means 16 previously described.

During this step, the acquired data correspond, for example, to time interval durations between two cycle starts.

According to a particular example of analysis of RR intervals, that is to say of the time between two consecutive R-waves of the heart rate, the data acquisition step consists, for example, in the acquisition of 1024 time intervals between two consecutive R waves.

This acquired data is for example stored in the storage memory device 13.

This step is illustrated in FIG. 3 by the reference 32.

According to a particular embodiment, the data acquisition step may be interrupted following the occurrence of one or more criteria related to the patient (heart rate, physical activity, temperature, etc.) or to an external event (time, telemetry control . . . ).

Step 22 is followed by a step 23 of preprocessing the acquired data.

Data preprocessing involves applying processing techniques to the signal for formatting it prior to frequency analysis. The preprocessing may for example consist of one or a combination of the following actions: filter, rectify, modulate, demodulate, oversample, downsample, interpolate . . . .

According to one particular example, during this step, the durations of the time intervals between two acquired R waves are converted into a constant time datum by interpolation and by resampling and a selection of a set of samples is carried out.

Resampling is carried out for example at a frequency of 4 Hz.

Another example of preprocessing of the acquired data is to correct the durations of the time intervals R-R during premature ventricular contractions also called ventricular extrasystoles.

During this preprocessing stage, a subset of the data acquired from the set of acquired data can also be selected.

This step is illustrated in FIG. 3 by the reference 33.

Step 33 is followed by step 34 to optimize the frequency analysis.

To do this, frequency bands on which the frequency analysis will be applied, in particular the Fourier transformation, are selected.

Figure 4:
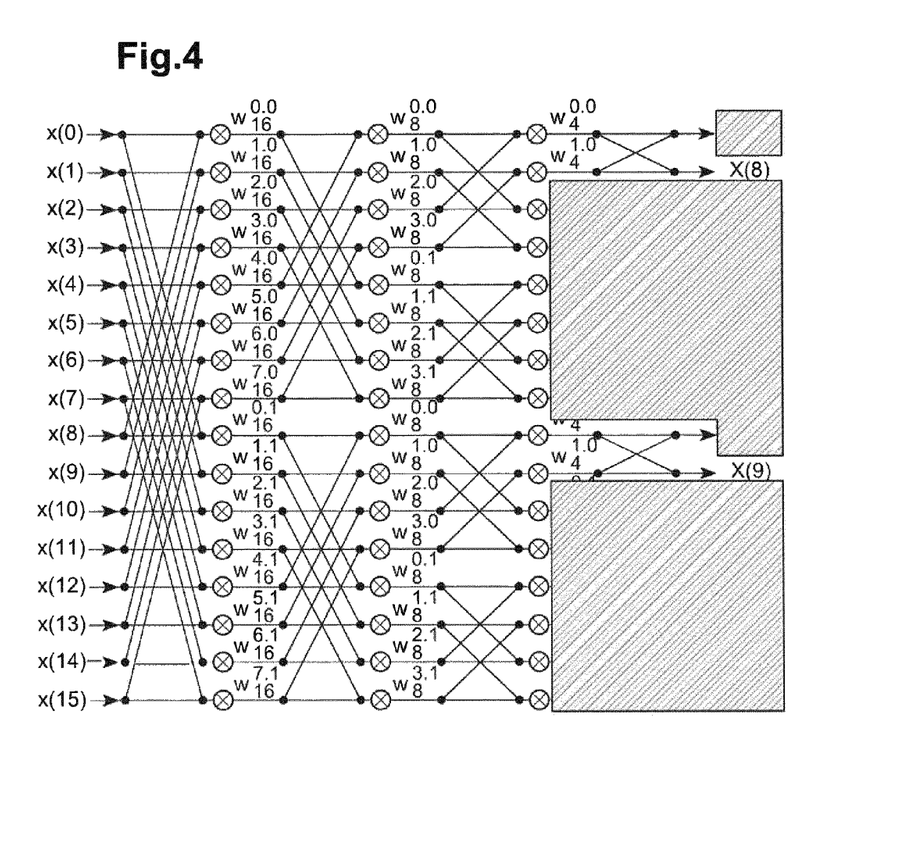
FIG. 4 is an optimization example of the frequency analysis according to the invention.

FIG. 4 illustrates an example of optimizing the frequency analysis by deleting frequency bands, the deleted frequency bands being represented in gray. Indeed, it has been observed that the relevant signal is present in only a few frequency bands. An example of a frequency band is the sinus frequency between 0.5 and 3 Hz.

By selecting frequency bands, the calculation of the frequency analysis is limited to the target frequency band(s) thus reducing the duration of the frequency analysis.

In addition, during this step and according to a particular embodiment, the frequency analysis is divided into a plurality of portions called elementary modules me in this particular embodiment.

For example, the analysis of an electrocardiogram requires the execution of 50,000 elementary modules me during 50,000 cardiac cycles.

According to another example, the analysis of an electromyogram requires the execution of 80,000 elementary modules me or 80,000 cycles, typically one cycle per second, that is 80,000 seconds (a little less than 24 hours).

This step is illustrated in FIG. 3 by the reference 34.

Step 24 is followed by a step 25 consisting in calculating a frequency analysis on said data by successive execution of the elementary portions or modules of the frequency analysis during periods of activity of the processing unit.

Thus, the data analysis is distributed over a plurality of cycles.

The means 17 for calculating the frequency analysis are able to execute the elementary portions or modules me of the frequency analysis.

This step is illustrated in FIG. 3 by the reference 35.

To implement the frequency analysis, the active implantable medical device may include means 19 for selecting an acquisition period of said data. The means for selecting an acquisition period may further comprise means for verifying conformity of predetermined criteria as previously described.

In addition, the data acquisition means 16 previously described can be implemented when the acquisition period is reached and the criteria are in accordance with predetermined values.

In addition, the active implantable medical device may comprise preprocessing means 20 for the acquired data adapted to resample the acquired time interval durations between two cycle starts according to a constant time data and to select a sequence of samples.

These preprocessing means 20 can also perform a selection of a subset of acquired data.

Finally, the active implantable medical device may comprise means 18 for optimizing frequency analysis capable of selecting at least one frequency band to be processed as previously described.

FIG. 3 also shows a sequencing of the operating state of the processing unit of the active implantable medical device during two cycles c and the execution of portions of the frequency analysis.

This figure illustrates two successive activations of the processing unit, the activation being performed for example synchronously relative to a cardiac event.

During an activation of the processing unit, it will be kept active during a period of activity p of a predetermined duration, for example 16 milliseconds.

During a first portion p1 of this period of activity, the processing unit performs standard processing functions.

During a second portion p2 of this period of activity, the processing unit performs a portion of the frequency analysis.

At the end of the period of activity of the processing unit, it goes into a standby state during a standby period v corresponding to the period of inactivity, this period extending until the end of the cycle c.

Thus, the calculating means 17 of a frequency analysis of an active medical device in accordance with the invention execute portions of the frequency analysis during the period of activity p2 of the processing unit.

In particular, the execution of the portions of the frequency analysis is performed after the execution of the standard processing functions, that is to say during the second portion p2 of the period of activity of the processing unit. In other words, the portions of the frequency analysis are executed at the end of the period of activity p of the processing unit.

According to an alternative embodiment, the calculating means of the active implantable medical device perform the portions of the frequency analysis at the beginning of the period of activity of the processing unit.

Thus, the invention advantageously makes it possible to use the periods of activity of the processing unit to perform the frequency analysis. In addition, the invention is based on the existing architecture of the implantable medical devices and does not compromise the execution of the main functions of the device namely by respecting the actual time required to perform the functions of the device. The invention thus makes it possible to optimize the resources required for the analysis, without significantly increasing the energy consumption, that is to say without decreasing the lifetime of the medical device, without compromising the real-time processing of the usual functions, and finally without modifying the material aspect, in particular without the addition of a dedicated processing circuit.

Figure 5:
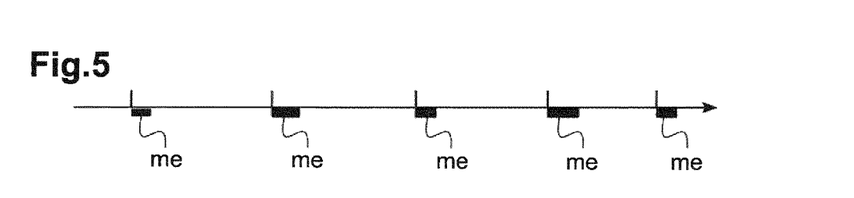
FIG. 5 is a first embodiment of the calculating means for a frequency analysis in accordance with the invention.

According to a first embodiment of the calculating means for a frequency analysis according to the invention illustrated in FIG. 5, the active implantable medical device comprises means 18 for optimizing the frequency analysis by splitting the frequency analysis into a plurality of elementary modules me. The portions executed by the calculation means are in this embodiment the elementary modules me resulting from the fact of splitting the frequency analysis.

These elementary modules can be of different sizes as illustrated in FIG. 5. Thus, the duration of execution of each elementary module me is different. However, the frequency analysis is split in such a way that the execution time of each elementary module is less than a predetermined duration, for example 2 milliseconds. Thus, the maximum execution duration of each elementary module me is known.

Of course, the fragmentation of the frequency analysis is performed according to the estimated duration of the remaining period of activity after the processing of the standard functions.

According to the invention, each elementary module me is executed successively during the periods of activity of the processing unit, in particular at each period of activity of the operating unit without interruption.

Alternatively, the elementary modules are executed during periods of non-consecutive operations of the operating unit. This embodiment is advantageous when the execution of the standard processing functions in a given cycle is performed for a duration that no longer allows the complete execution of an elementary module me during the activation period of the processing unit. To do this, the duration of the second portion of the period of activity of the processing unit is calculated, if it is less than the maximum duration of execution of an elementary module me, then the means 17 for calculating the frequency analysis will wait for the next period of activity of the processing unit to execute the portion of the frequency analysis.

Figure 6:
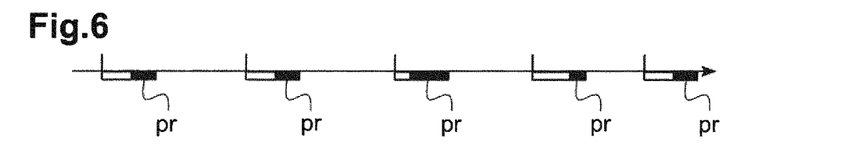
FIG. 6 is a second embodiment of the calculating means for a frequency analysis according to the invention.

According to a second embodiment of the calculating means for a frequency analysis according to the invention illustrated in FIG. 6, the calculating means execute a portion pr of the frequency analysis after the execution of the standard functions, the execution of the frequency analysis continues until the end of the period of activity of the processing unit.

Thus, the frequency analysis starts after the execution of the standard processing functions and continues for all the remaining duration of the activity period p of the processing unit as illustrated in FIG. 6.

According to this embodiment, the execution duration of each portion of the frequency analysis during the activation periods of the processing unit is different since this portion pr is dependent on the remaining time of the period of activity p2 of the processing unit after performing standard functions.

This embodiment has the advantage of using the entire period of activity of the processing unit and thus of optimizing the execution time of the frequency analysis.

Figure 7:
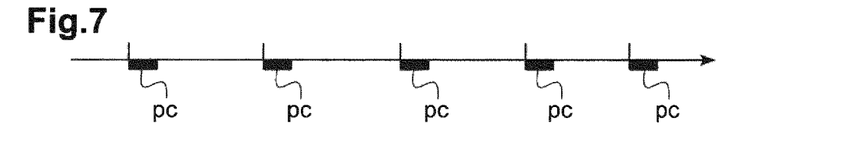
FIG. 7 is a third embodiment of the calculating means for a frequency analysis according to the invention.

According to a third embodiment of the calculating means for a frequency analysis in accordance with the invention, illustrated in FIG. 7, the calculating means successively execute, at each period of activity of the processing unit, a portion pc of the frequency analysis for a predetermined duration.

According to this embodiment, the execution duration of each portion pc of the frequency analysis is determined, and for example this duration is 2 milliseconds. At the end of this period, the execution of the frequency analysis is stopped.

The calculating means can execute the portion pc of the frequency analysis preferably after the execution of the standard functions. However, alternatively, the portion pc of the frequency analysis can be executed at the beginning of the activity period p of the processing unit.

Figure 8:
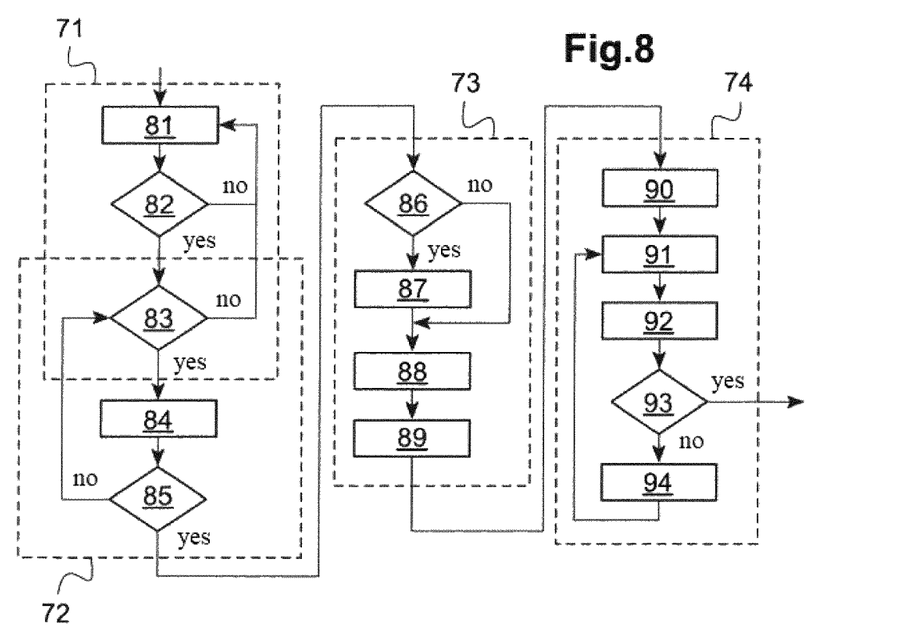
FIG. 8 illustrates an example of implementing an analysis of intervals R-R of a patient's heart rate.

FIG. 8 illustrates an exemplary implementation according to the invention of an analysis of the intervals R-R of a patient according to a particular frequency analysis, namely a Fourier transformation.

Figure 2:
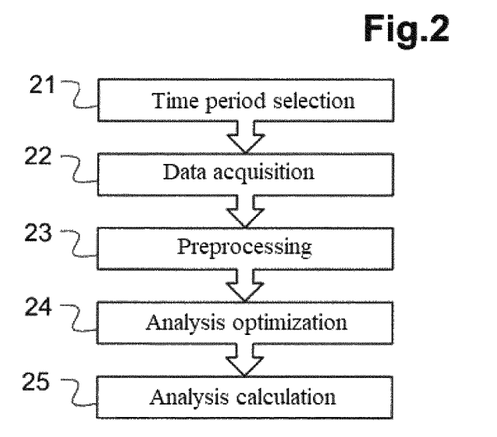
FIG. 2 is a method for data frequency analysis according to the invention.
Figure 3:
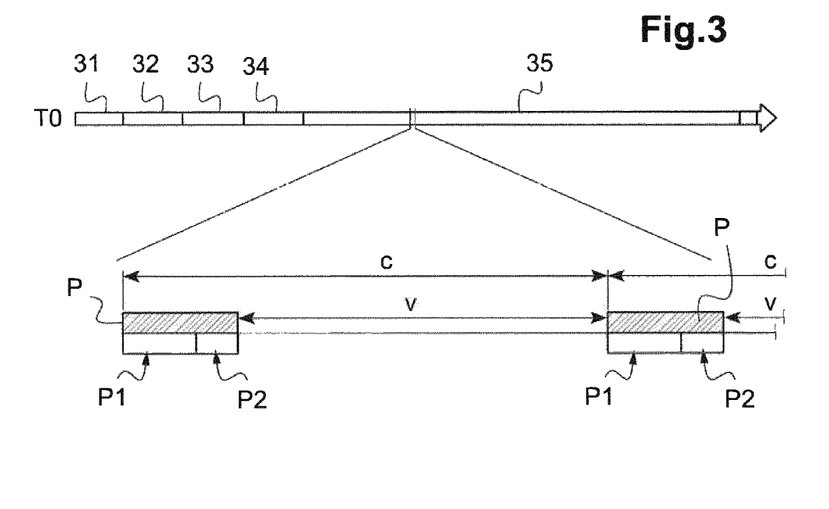
FIG. 3 sequentially illustrates the frequency analysis according to the invention.

This implementation is based on a step 71 of selecting the acquisition period in accordance with step 21 of FIG. 2, then of a data acquisition step 72 in accordance with step 22 of FIG. 2. then a preprocessing step 73 in accordance with step 23 of FIG. 2 and finally a step 74 of calculating a frequency analysis on data acquired in accordance with step 25 of FIG. 2.

It will now be described in detail each of these steps during their implementation for the analysis of intervals R-R using a Fourier transformation.

The steps described below are executed sequentially.

The step 71 consisting in selecting the acquisition period is broken down into sub-steps 81 to 83.

The first step 81 is a waiting step of the predetermined period of time at which the acquisition of the data from the patient is to take place.

Step 81 is followed by a test step 82 to determine if the acquisition time period is reached.

If the acquisition time period is not reached, the algorithm goes to step 81 as previously described.

In the opposite case, then step 82 goes to step 83 making it possible to test predetermined criteria, in particular the physiological conditions of the patient with respect to predetermined values.

If all the predetermined criteria gathered from the patient do not conform to the predetermined values, the algorithm then goes to step 81 as previously described, in particular in order to wait for the next acquisition time period.

In the opposite case, step 83 then goes to the data acquisition step 84, these data being the durations of the intervals R-R during a given time period and the recording of these durations.

Step 84 then goes to step 85 to determine if the recording of the data is complete.

Steps 84 and 85 are sub-steps of the step 72 of data acquisition.

If the record is incomplete, then the algorithm goes to step 83 previously described.

Indeed, the acquisition and recording of data are stopped when a predetermined criterion captured from the patient do not comply with the determined value. If this is the case, a new acquisition time period will be expected to complete the acquisition of the data, this new period may be the following day.

On the other hand, if the physiological activity of the patient is such that the criteria are fulfilled during the entire acquisition period, then the acquisition ends when the predefined acquisition period is over or the storage capacity is reached.

In this case, step 85 is followed by step 86 which is a first sub-step of step 73 of preprocessing the acquired data.

Step 86 is a test step for determining whether premature ventricular contractions are detected.

If such contractions are detected, then step 86 is followed by a step 87 consisting in correcting the durations of the intervals R-R during which premature ventricular contractions have been detected.

This step 87 is followed by a step 88 consisting in resampling the durations of the intervals R-R into a temporal information compatible with the calculation of the Fourier transform, for example by sampling at a frequency of 4 Hz.

During step 86, if no premature ventricular contraction is detected, then step 86 goes to step 88 consisting in resampling the durations of the intervals R-R.

Step 88 goes to step 89 consisting in selecting a set of samples, in particular $2^n$ samples which will be processed by the Fourier transform, for example 1024 samples, are selected.

The following steps constitute sub-steps of the step 74 consisting in calculating a frequency analysis on samples by successive execution of portions of the Fourier transform, in particular of elementary modules.

To do this, step 89 goes to step 90 consisting in initializing the Fourier transform and the counter i to 0.

Step 90 continues in step 91 consisting in waiting the completion of the standard processing functions by the processing unit during the activity period.

When the end of execution of the standard processing functions is detected, step 91 goes to step 92 consisting in calculating a portion of the Fourier transformation, in particular of an elementary module.

This step 92 goes to step 93 consisting in testing the counter i to determine whether the entire Fourier transform has been processed, in particular if all the elementary modules have been executed.

The number of elementary modules is defined in this example by the variable m.

If the counter i is smaller than the number of elementary modules m, then the algorithm goes to step 94 by incrementing the counter i by the value 1. Then the algorithm goes to step 91 previously described in order to execute the next transformation portion, including the following elementary module.

When all the elementary modules of the Fourier transformation are executed, the counter i is equal to the variable m during step 93, then the algorithm ends and the result of the Fourier transformation can be exploited and the algorithm of FIG. 8 can be executed again.

The active implantable medical device according to the invention can be implemented for frequency analysis of different types of signals or data, in particular:

for the analysis of heart rate variability by extracting low frequency and high frequency components in the heart rate, for the analysis of the frequency of the electroneurogram from a characterization of fiber types, for the analysis of the arterial pressure oscillations, for example the Traube-Hering-Mayer oscillation, for the analysis of respiratory disorders, for example the Cheyne-Stokes breathing, for the analysis of gastric contractions, for the analysis of data of an electromyogram, for example for the discrimination between the target signal and the muscular activity, and for the analysis of remote fields, for example for the discrimination between the target signal and the remote noise.

In a particular implementation of the invention, the frequency analysis is performed on the variability of the heart rate. This allows, among other things, to detect physiological dysfunctions. One of these dysfunctions concerns an alteration of the sympathovagal balance, representing the balance between the parasympathetic autonomic system (vagus nerve) and the sympathetic system. This imbalance is recognized as being a predictive factor of mortality in certain cardiovascular pathologies, in particular after myocardial infarction.

The variability of the heart rate can be appreciated through various parameters. These parameters may relate to the time domain based on power measurements in predefined bands such as high frequency (HF) and low frequency (LF) bands, etc.

The high frequency/low frequencies (LF/HF) ratio is considered as being the most representative value of the sympathovagal balance (SVB).

In the clinical field, the Holter technique allows the recording of the cardiac activity of a subject for a period of time for example 24 or 48 hours and allows an analysis of the subject's heart rate.

Figure 9:
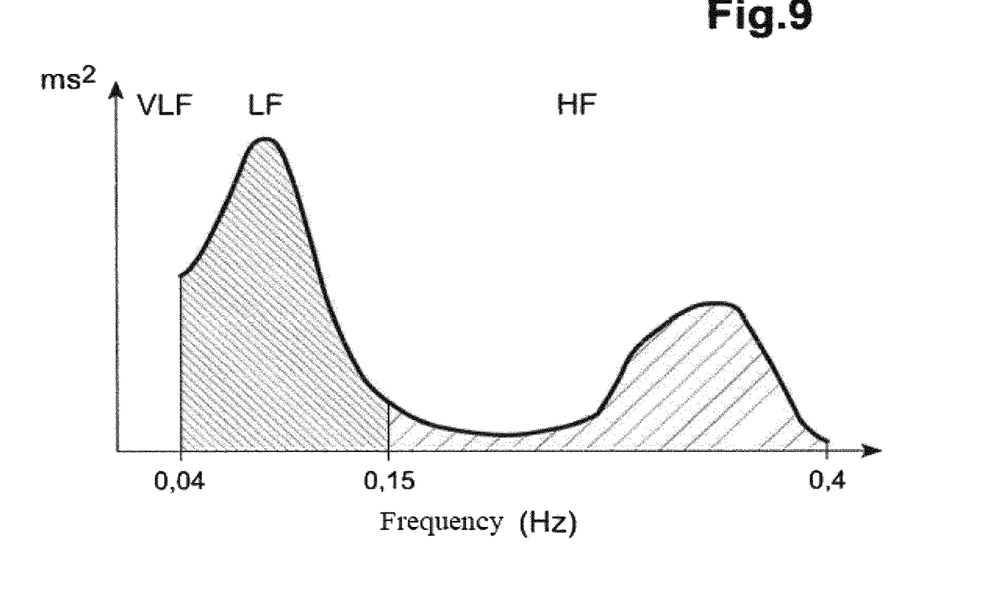
FIG. 9 illustrates frequencies on which the frequency analysis in accordance with the invention can be performed.
Figure 10:
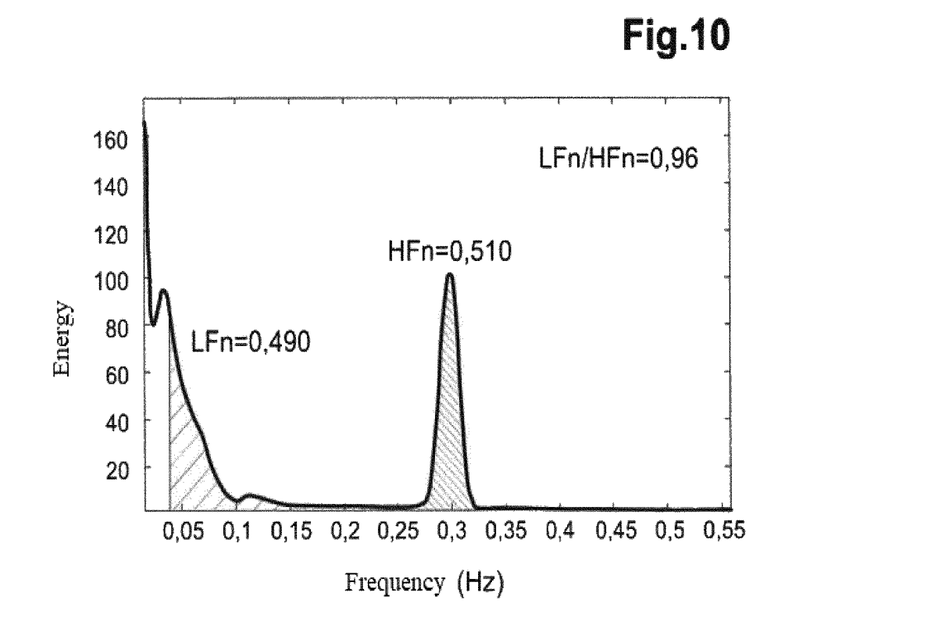
FIG. 10 illustrates frequency ratios on which the frequency analysis in accordance with the invention can be performed.

FIGS. 9 and 10 illustrate frequencies on which the frequency analysis applied to the rhythmic activity of the heart according to the invention can be applied.

The analysis of the frequency domains is standardized as shown in FIG. 9. Thus, the high frequencies (HF) in the adult concern the frequency band of 0.15 to 0.4 Hz and the low frequencies (LF) concern the frequency band of 0.04 to 0.15 Hz. High frequencies are an indicator of the parasympathetic activity and low frequencies mainly reflect the sympathetic activity. The LF/HF ratio is a global indicator of the sympathovagal SVB balance.

The sympathovagal balance is often estimated from the power in these two frequency bands and the values can be standardized according to the following formulas:

$$LF = \int_{0.04}^{0.15} S(f) df$$

$$HF = \int_{0.15}^{0.4} S(f) df$$

The power of the signal can then be extracted from the frequency analysis as illustrated in FIG. 10.

Heart rate variability analysis can also be performed on other parameters, including temporal data (RMSSD, SDNN, SDANN, etc.), geometric values such as the density NN distribution, the Lorenz curve, and nonlinear measurements such as fractal approaches or the so-called Poincaré curve. All of these analyzes can be implanted in an implantable medical device and implemented according to the described invention.

The invention claimed is:

1. An active implantable medical device comprising:
a memory having instructions stored thereon and a processing unit able to be alternately operated during a determined period of activity and on standby during a period of standby in a cyclical manner;
wherein the processing unit is configured to execute the instructions to implement operations comprising:

acquiring data related to physiological or physical activity;

calculating a frequency analysis of the acquired data by fractioning the frequency analysis into a plurality of portions each having an execution time, wherein two or more of the plurality of portions have different execution times, and wherein the frequency analysis is fractioned such that the execution time of each portion is less than a predetermined duration;

successively executing the plurality of portions of the frequency analysis during periods of activity of the processing unit; and providing stimulation responsive to the frequency analysis indicating the presence of a cardiac event.

2. The active implantable medical device of claim 1, wherein the instructions are configured to cause the processing unit to calculate during the period of activity of the processing unit after execution of standard processing functions executed during the period of activity of the processing unit.

3. The active implantable medical device of claim 2, wherein the instructions are configured to cause the processing unit to execute a portion of the frequency analysis after execution of standard processing functions executed until the end of the period of activity of the processing unit.

4. The active implantable medical device of claim 1, wherein the instructions are further configured to cause the processing unit to select at least one frequency band to be processed.

5. The active implantable medical device of claim 1, wherein the instructions are further configured to cause the processing unit to select a period of acquisition of said data.

6. The active implantable medical device of claim 5, wherein the instructions are further configured to cause the processing unit to verify the conformity of predetermined criteria.

7. The active implantable medical device of claim 5, wherein the instructions are further configured to cause the processing unit to acquire data when the period of acquisition is reached and the criteria are in accordance with predetermined values.

8. The active implantable medical device of claim 1, wherein the instructions are further configured to cause the processing unit to detect a determined physiological event external to the device and start the period of activity a specific physiological event is detected.

9. The active implantable medical device of claim 1, wherein the instructions are further configured to cause the processing unit to preprocess the acquired data.

10. The active implantable medical device of claim 9, wherein the instructions are further configured to cause the processing unit to interpolate and resample the acquired data.

11. The active implantable medical device of claim 1, wherein the instructions are further configured to cause the processing unit to calculate the frequency analysis in a final portion of the period of activity of the processing unit.

12. The active implantable medical device of claim 1, wherein the frequency analysis is a Fourier transform.

13. An active implantable medical device comprising:
a memory having instructions stored thereon and a processing unit able to be alternately operated during a determined period of activity and on standby during a period of standby in a cyclical manner;
wherein the processing unit is configured to execute the instructions to implement operations comprising:
acquiring data related to physiological or physical activity;
calculating a frequency analysis of the acquired data by fractioning the frequency analysis into a plurality of portions having varying execution times, wherein the execution time of each of the plurality of portions is less than a predetermined duration and is determined based on an estimated amount of time remaining after the processing unit executes standard processing functions in a corresponding period of activity, and wherein two or more of the plurality of portions have different execution times;
successively executing the plurality of portions of the frequency analysis during periods of activity of the processing unit; and
providing stimulation responsive to the frequency analysis indicating the presence of a cardiac event.

* * * * *